United States Patent [19]
Seiter et al.

[11] Patent Number: 5,121,636
[45] Date of Patent: Jun. 16, 1992

[54] SURFACE ENERGY METER

[75] Inventors: Charles H. Seiter, Healdsburg; Roger P. Woodward, San Francisco, both of Calif.

[73] Assignee: WDA Contracts Corporation, South San Francisco, Calif.

[21] Appl. No.: 774,533

[22] Filed: Oct. 8, 1991

[51] Int. Cl.$^5$ .................................... G01N 13/02
[52] U.S. Cl. ................................... 73/64.48
[58] Field of Search ........................... 73/64.4

[56] References Cited

U.S. PATENT DOCUMENTS 4,228,677  10/1980  Olsson et al. .............. 73/64.4
4,650,588   3/1987  Diebold ................. 73/64.4 X Primary Examiner—Hezron E. Williams
Assistant Examiner—Michael Brock
Attorney, Agent, or Firm—Whitham & Marhoefer

[57] ABSTRACT

A surface energy meter (10) includes a probe (18) having two spaced apart electrodes (38 and 40) with a centrally located fluid dispensing head (36). When a fluid of known surface tension is dispensed onto a material (22) having unknown surface energy, the surface energy is determined by the volume of a fluid drop (42) which bridges between electrodes (38 and 40). The volume of the fluid drop (42) is closely regulated using a stepper motor (24) and by tracking the number of steps and volume dispensed per step required for the fluid drop (42) to expand to a point where the electrodes (38 and 40) are bridged. When a fluid of unknown surface tension is to be tested, materials having known surface energies are used.

15 Claims, 2 Drawing Sheets

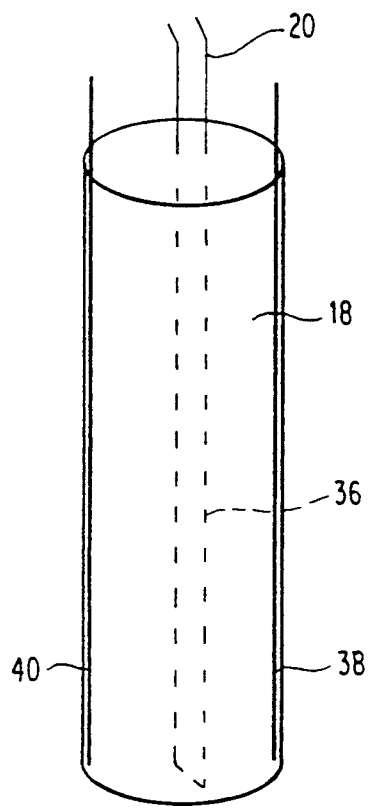
FIG. 2
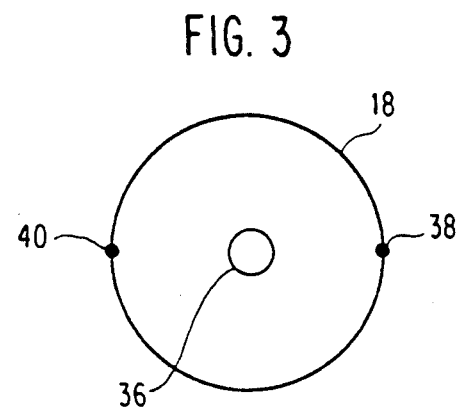
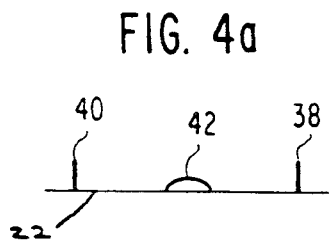
FIG. 4a
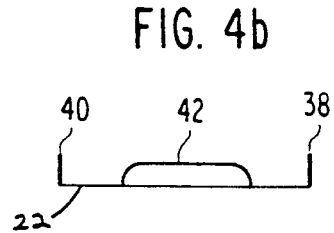
FIG. 4b
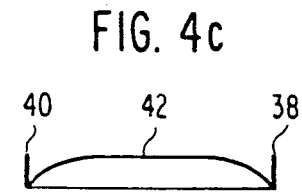
FIG. 4c
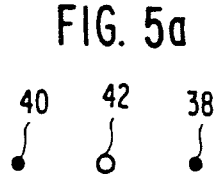
FIG. 5a
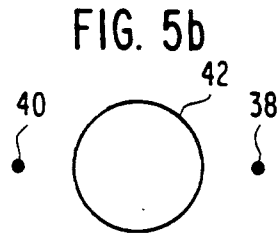
FIG. 5b
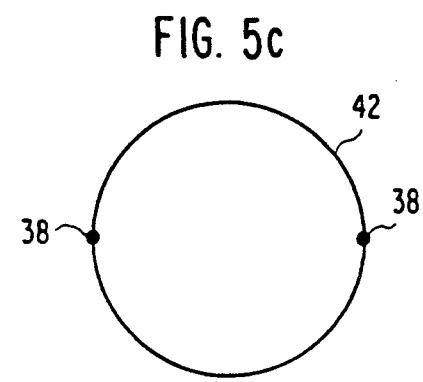

SURFACE ENERGY METER

BACKGROUND OF THE INVENTION

1. Field of the Invention

The present invention is generally related to instruments which can measure the surface energy of a material and, more particularly, to a compact surface energy meter which can perform surface energy measurements in an automated fashion.

2. Description of the Prior Art

Knowledge of the surface energy of a material is particularly important in the plastics field. For example, the ability to print or coat a material is highly dependent on the surface energy of the material. In addition, the surface energy of the material will determine its suitability for medical or biotechnology applications. The surface energy of a material is a measure of the thermodynamic energy needed to increase surface area and is measured in dynes/cm. For historical reasons, the same parameter in liquids is called surface tension, rather than surface energy. Surface energy measurements have been routinely made for several years by a variety of different techniques.

One method of making surface energy measurements involves optically determining the contact angle of a drop of pure water on the surface of the material of interest. Since the surface tension of pure water is 72 dynes/cm at 25° C., knowledge of the contact angle can yield the surface energy of the material from the Girifalco-Good-Fowkes-Young equation which is set forth in Equation 1 below:

$$\cos\theta = -1 + 2\left(\frac{\gamma_S}{\gamma_L}\right)^{\frac{1}{2}} - \frac{\pi_{SV}}{\gamma_L}$$

The Girilalco-Good-Fowkes-Young equation is a thermodynamic expression which relates solid surface energy $\gamma_S$ to liquid tension $\gamma_L$ and contact angle $\theta$, with a small correction term for vapor pressure $\pi_{SV}$, and is discussed in *J. Phys. Chem.* 61: 904 (1957), which is herein incorporated by reference.

Another method of making surface energy measurements involves the use of a plurality of fluids, each with a known surface tension, where the technician sequentially smears different fluids on the surface of the material of interest. The surface energy of the material is determined when one of the fluids is found to just form a continuous film.

Still another method of making surface energy measurements involves dipping the material into a fluid of known surface tension and then weighing the material. The weight of fluid which adheres to the surface of the material is then used to provide a measure of the surface energy of the material.

A problem with the prior art methods of making surface energy measurements is that they rely heavily on the judgement and ability of skilled technicians. Providing a surface energy meter which requires minimal training for use, but which can provide accurate and reliable data, would be very beneficial in the plastics field.

SUMMARY OF THE INVENTION

It is therefore an object of the invention to provide an automated surface energy meter which is easy to use and which provides reliable measurements.

It is another object of the invention to provide a surface energy meter which can be used to detect the surface energy of a material with a fluid having a known surface tension or which can be used to detect the surface tension of a fluid with a material having a known surface energy.

It is yet another object of the invention to provide a surface energy meter which utilizes electrical sensing to determine surface energy of a material.

It is still another object of the invention to provide a surface energy meter which is compact and portable.

According to the invention, a digital surface energy meter includes a fluid chamber, a pump, a microprocessor, a control panel, and a probe. The probe has two separated electrodes and a fluid outlet therebetween for dispensing an electrically conductive fluid onto the surface of a material. The rate which the electrically conductive fluid is dispensed is controlled by a stepper motor in the pump. When fluid is dispensed onto the surface of the material, a drop forms between the electrodes and expands as the volume of the drop increases. When the drop bridges the two electrodes, a current is conducted through the electrically conductive fluid and the presence of the current acts as a switch which halts the operation of the stepper motor.

At the time the drop bridges the two electrodes, the volume of fluid dispensed can be accurately determined from the number of steps of the stepper motor. The microprocessor uses the volume of fluid dispensed to determine surface energy of an unknown material or surface tension of an unknown fluid. To speed operation, the microprocessor includes a look-up table which relates volume to surface energy. When surface energy of an unknown material is being measured, fluids of known surface tension are dispensed from the probe. Because plastic materials can have a wide range of surface energies, it is preferable to use a number of different fluids, each of which is optimum for a specific range of surface energies. Identification of the fluid being used and its surface tension characteristics can be performed using a built-in bar code reader on the surface energy meter. When surface tension of an unknown fluid is being measured, the unknown fluid is dispensed from the probe onto materials of known surface energy.

BRIEF DESCRIPTION OF THE DRAWINGS

The foregoing and other objects, aspects and advantages will be better understood from the following detailed description of a preferred embodiment of the invention with reference to the drawings, in which:

FIG. 2 is a side view of the probe used in the surface energy meter;

FIG. 3 is a bottom view of the probe used in the surface energy meter;

FIGS. 4a-c are sequential side views of a drop expanding on a surface to electrically connect the electrodes of the probe of the surface energy meter; and FIGS. 5a-c correspond with FIGS. 4a-c and are sequential top views of the drop expanding on the surface.

DETAILED DESCRIPTION OF THE PREFERRED EMBODIMENTS OF THE INVENTION

Figure 1:
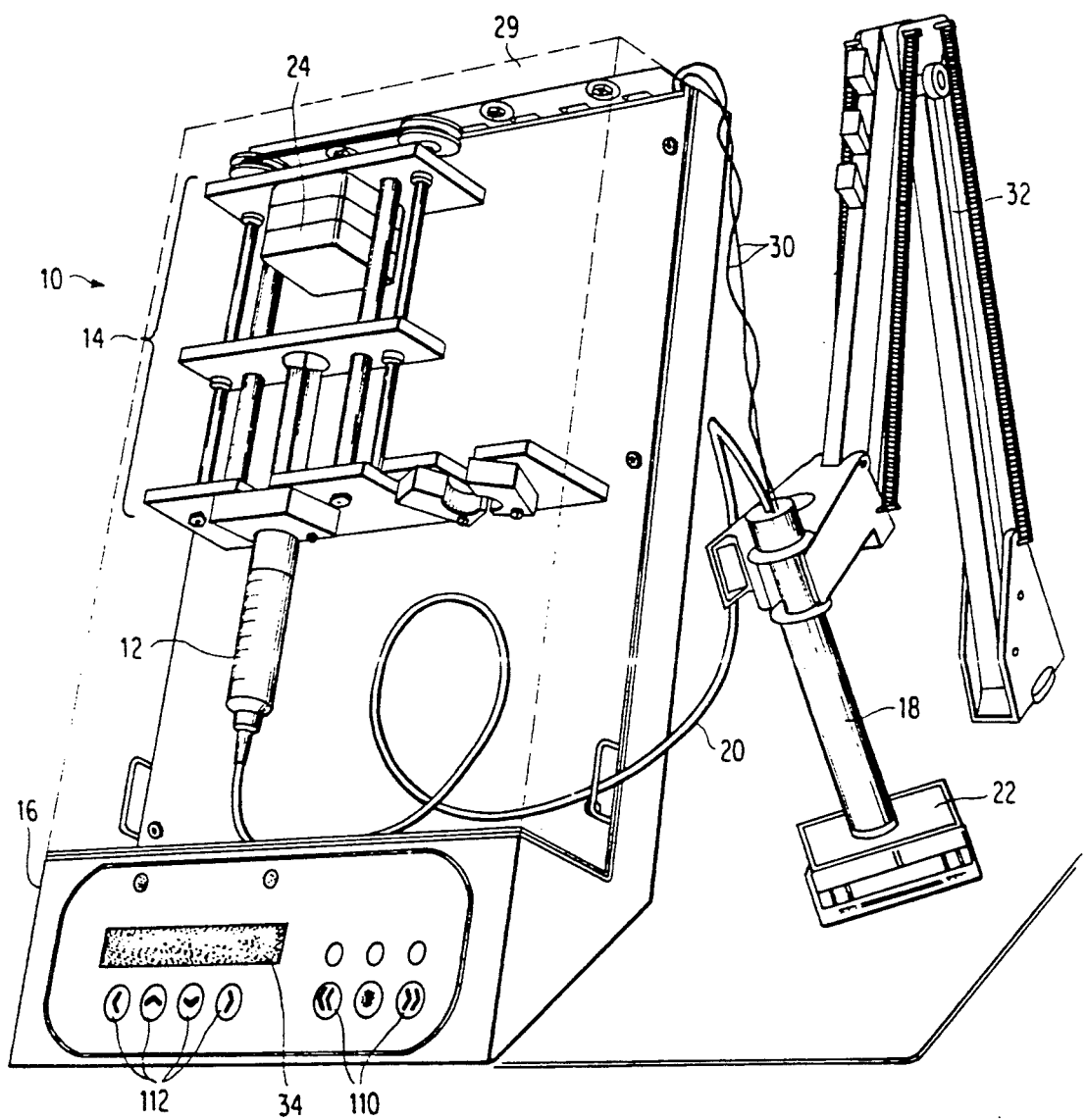
FIG. 1 is an isometric view of the surface energy meter according to the present invention.

Referring now to the drawings, and more particularly to FIG. 1, there is shown the digital surface energy meter 10 of the present invention which includes a syringe 12, a pump 14, a control panel 16, and a probe 18. The syringe 12 contains an electrically conductive fluid which is pumped to the probe 18 via conduit 20 and onto the surface of a material 22. The pump 14 is preferably driven by a stepper motor 24 which sequentially moves plate 26 downward on stem 28 of the syringe 12. Precise volumes of fluid are delivered with each step of the motor 24 where the volumes depend on the size syringe 12 which is used and degree of movement of plate 26 per step. Other pumps capable of metering out precise volumes of fluid could also be used within the practice of the invention including electronically controlled pumps, and clock-drive-type pumps. A clear plastic cover 29 can be positioned over the pump 14 and syringe 12 to provide environmental protection.

Probe 18 includes two electrodes, discussed in detail below, which are electrically connected to the surface energy meter 10 via conductive wires 30. While the probe 18 can be fitted on a stand 32, it is preferably of a size and has the flexibility in terms of conduit 20 length and wire 30 length which allows it to be positioned on any flat surface. Those skilled in the art will recognize that the probe 18 and surface energy meter 10 unit can be readily adapted for hand-held use in the field where a battery powers the surface energy meter 10 and the technician holds the probe 18 against the surface of interest. In a preferred embodiment, the probe 18 is one centimeter in diameter; however, the probe 18 could be made smaller or larger for accommodating a variety of different surfaces.

The surface energy meter 10 is preferably microprocessor controlled. Control panel 16 allows entry of fluid, material, and other information into the microprocessor inside the surface energy meter 10, as well as displays surface energy measurement results in display area 34. The double arrow keys 110 on control panel 16 allow the operator to drive the stepper motor rapidly backwards (<<) and forwards (>>). The microprocessor should also be programmable to drive the stepper motor at a prescribed rate. The arrow keys 112 under the display area 34 allow the operator to change the values presented in program menus used for programming the surface energy meter 10.

FIGS. 2 and 3 show the probe 18 has a centrally located fluid dispensing head 36 connected to conduit 20. Two electrodes 38 and 40 are located on opposite sides of the probe 18. The electrodes 38 and 40 may extend beyond the probe 18 bottom or be even therewith. The function of the electrodes 38 and 40 is to provide a means of sensing the presence of a fluid droplet. Fluid dispensed by the fluid dispensing head 36 is made electrically conductive so that current passes between electrodes 38 and 40 when the fluid droplet provides an electrically conductive pathway between them.

FIGS. 4a–c and corresponding FIGS. 5a–c provide a description of the operation of the probe 18 of the surface energy meter 10 and are best understood with reference to FIGS. 1–3. FIGS. 4a and 5a show that at the beginning of a measurement run, the fluid dispensing head 36 deposits a controlled volume of fluid 42 on a surface 22 at a central location between the probes 38 and 40. FIGS. 4b and 5b show that the diameter of the fluid drop 42 increases as more fluid is pumped onto the material surface 22. FIGS. 4c and 5c show that the diameter of the fluid drop 42 will ultimately become large enough to bridge electrodes 38 and 40 as more fluid is pumped onto surface 22. When the fluid drop 42 bridges electrodes 38 and 40, the stepper motor 24 is shut off. The volume of the fluid drop 42 required to bridge the electrodes 38 and 40 can be precisely determined by knowing the number of steps required by the stepper motor 24 to bridge the electrodes 38 and 40 and the volume dispensed per step.

In the case where the surface energy meter 10 is to be used to determine the surface energy of an unknown solid, a volume of a fluid having a known surface tension is pumped onto the unknown solid until the electrodes 38 and 40 are bridged. Stored in the microprocessor prior to testing are values which relate stepper motor counts (a volume measurement) for the particular fluid having the known surface tension being used to the surface energy of at least two known solids which preferably have correspondingly expected higher and lower surface energies than the solid under investigation (although having higher and lower surface energies is not required). The volume of fluid having the known surface tension which was dispensed on the solid having the unknown surface energy is then used to calculate the surface energy of the unknown solid by first determining a variable X according to Equation 2 as follows:

$$X = \frac{V_{Low} - V_{Meas}}{V_{Low} - V_{High}} \qquad \text{Eq. 2}$$

where $V_{Low}$ is the volume in stepper motor counts of the fluid having the known surface tension which is required for bridging the electrodes when a solid having a low surface energy is measured, $V_{High}$ is the volume in stepper motor counts of the fluid having the known surface tension which is required for bridging the electrodes when a solid having a high surface energy is measured, and $V_{Meas}$ is the volume in stepper motor counts of the fluid having the known surface tension which was required for bridging the electrodes for the solid under investigation. After the variable X is calculated according to Equation 2 above, the surface energy of the solid under investigation is computed according to Equation 3:

$$S.E.(dynes/cm) = E_{Low} + (E_{High} - E_{Low}) \cdot x \qquad \text{Eq. 3}$$

where $E_{Low}$ is the known surface of the low surface energy solid used for $V_{Low}$, and $E_{High}$ is the known surface energy of the high surface energy solid used for $V_{High}$. The EXAMPLE, discussed below, presents test data where the above operation and equations were successfully used for determining the surface energy of test surfaces.

Likewise, in the case where the surface energy meter 10 is to be used to determine the surface tension of a fluid, the fluid with unknown surface tension is pumped onto a surface of a material having a known surface energy until the electrodes are bridged. The surface tension can then be calculated from the volume of the fluid having unknown surface tension required to bridge the electrodes 38 and 40. Specifically, volume values in terms of stepper motor counts for two fluids having known surface tensions which are preferably higher and lower than the expected surface tension of the unknown fluid (although having higher and lower surface tensions is not required) and which relate the two fluids to a surface having a known surface energy are used in a calculation like equation 2 after the volume value for the fluid having unknown surface tension is determined on the surface having a known surface energy. Subsequently, the surface tension is determined in a calculation like that of equation 3 where the surface tensions of the known fluids are combined with a variable which considers the volume required for the fluid having unknown surface tension to bridge the electrodes when a solid of known surface energy is used.

In a preferred embodiment of the invention, a microprocessor in the surface energy meter 10 can include a look-up table which relates volume information to surface energy or tension. In this manner, the speed of determining a surface energy or surface tension measurement will be increased since calibration runs with fluids having known surface tensions and solids having known surface energies would not need to be performed each time the surface energy of an unknown solid or the surface tension of an unknown fluid are to be determined. The calibration runs would be storable in memory and would only need to be performed periodically.

The principle of operation can be understood by contrasting a test where a drop of water is used to determine the surface energy of an untreated polyethylene material with a test where a drop of water is used to determine the surface energy of a polyethylene material that has been subjected to a plasma or corona discharge. In each test, the water would include a small amount of salt for conductance purposes. If the water is pumped onto the untreated polyethylene surface, the water will form a very tall drop with a contact angle of 90° or more, a condition sometimes referred to as "beading" up. In this situation, a large amount of water would need to be dispensed before a fluid drop 42 having sufficient diameter to bridge electrodes 38 and 40 is formed. The large volume of water required to bridge the electrodes 38 and 40 would correspond to the untreated polyethylene having a low surface energy. By contrast, when the water is pumped onto the plasma or corona treated polyethylene surface, which are two common ways to make a polyethylene surface "printable" with water-based inks, the water will form a very flat drop with a contact angle of 10° or less. In this situation, a relatively small volume of water is required to obtain a fluid drop 42 of sufficient diameter to bridge electrodes of 38 and 40. The small volume of water required to bridge the electrodes 38 and 40 would correspond to a high surface energy.

Ideally, fluids having higher contact angles on the surface of interest are better for detecting the surface energy. This is because very low contact angles are not easily repeatable. Since no single fluid is known which will be capable of having a suitable contact angle on all surfaces, it is preferred to have a large number of fluids with different known surface tensions when determining the surface energy of a material of interest. In a preferred embodiment, five or more fluids will be used in the surface energy meter 10 where the surface tension of each of the fluids is selected to be suitable for accurately testing the surface energy of materials within a specific range of surface energies. The surface tensions of each of the fluids can be indicated on the syringe 12 using a bar-code so that the technician is not required to input the surface tension each time a test performed. A bar-code reader could be attached to or built-in the surface energy meter 10 so that each time a different fluid of known surface tension is placed in the surface energy meter 10, the microprocessor automatically considers the surface tension when determining the surface energy of the material under investigation. If a plurality of fluids having known surface tensions are to be used, a means for assuring that the pump 14 empties all remaining fluid of a prior syringe 12 stored in conduit 20 before the new fluid is used in a test. Likewise, if the surface tension of an unknown fluid is to be determined, it would be advantageous to have a plurality of materials, each of which has a known surface energy that is suitable for determining surface tensions within different ranges. In addition, if an unknown fluid is to be tested, it must first be made electrically conductive by adding a small amount of salt.

A number of fluids, each of which has a different known surface tension, can be made simply by combining different ratios of known fluids. For example, a mixture of isopropanol and water can be easily adjusted to produce a test fluid ranging between 30 dynes/cm and 72 dynes/cm, which are the surface tensions of pure isopropanol and pure water, respectively. In a particular embodiment, by mixing 90 gms of water with 10 gms of isopropanol, a fluid with a surface tension of 55 is produced. Solutions are best prepared using ingredient weights rather than volumes because weight can be specified with greater accuracy than volumes, especially for large quantities. In a preferred embodiment, the solutions are adjusted to approximately 0.0005 M NaCl for detecting a sharp conductivity change and may be provided with trace amounts of a blue dye for the technician to observe the spreading of the fluid drop under the probe. Other salts could be used instead of NaCl with the only requirement being that the amount of salt be large enough to promote electrical conductivity between the electrodes 38 and 40, but small enough not to interfere with the surface energy measurement. Isopropanol and water mixes are inexpensive and present minimal corrosion and plastics compatibility problems; however, it should be understood that other organic compounds that are soluble in water can be used in like manner. For example, water could be mixed with formamide, dimethyl formamide, and acetone to make a series of solutions with surface tensions of different values. In addition, formamide might be combined with water/isopropanol formulations to fine tune the mixtures to achieve particular surface tension numbers. Moreover, the range of surface tensions for the test fluids can be expanded beyond isopropanol/water mixtures. For example, hexane, with a surface tension of 18 dynes/cm can be mixed with n-butanol, at 25 dynes/cm and toluene at 29 dynes/cm to obtain a range of mixtures below 30 dynes/cm. Potassium carbonate solutions, with a surface tension of 85 dynes/cm for a 2M concentration, may be used to obtain test fluids with surface tension above 72 dynes/cm.

EXAMPLE

Mylar with no calendaring agents and glass treated with a hydrocarbon plasma were used as solids with known surface energies. The surface energies of the materials were determined to be 44 dynes/cm for the Mylar and 60 dynes/cm for the plasma treated glass by repeated tests with wetting solutions according to the established prior art technique of smearing a series of wetting solutions on the surface of the materials. A plasma was then used to produce two treated glass surfaces with unknown surface energies which were below 60 dynes/cm (the plasma treatment conditions used to create the known surface were modified to create a glass with lower surface energy). The fluid used in the experiments for determining the surface energies was water with 0.005 M NaCl and a trace amount of blue dye, which had a known surface tension of 70 dynes/cm. The measured volume in steps for the 60 dynes/cm plasma treated glass surface was 219, while the measured volume in steps for the 44 dynes/cm Mylar surface was 420. One of the plasma treated glass test surfaces had a fluid volume value of 316 steps which corresponds to a surface energy value of 52 dynes/cm, and the other plasma treated glass test surface had a fluid volume value of 443 steps which corresponds to a surface energy value of 42 dynes/cm. These surface energy values were determined to be correct using the prior art technique of smearing a series of fluids having known surface tensions on the test surfaces.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A surface energy meter, comprising:
    a vessel for holding an electrically conductive fluid;
    at least two spaced apart electrodes which can be bridged by said electrically conductive fluid;
    a means for dispensing said electrically conductive fluid from said vessel onto a surface of a material at a point centrally located between said two spaced apart electrodes;
    means for determining a volume of said electrically conductive fluid required to be dispensed onto said surface of said material to bridge said two spaced apart electrodes and provide an electrical pathway therebetween; and
    means for relating said volume of said electrically conductive fluid to a surface energy of said material and a surface tension of said electrically conductive fluid.
2. A surface energy meter as recited in claim 1 wherein said means for dispensing includes a pump.
3. A surface energy meter as recited in claim 2 wherein said pump is electronically controlled.
4. A surface energy meter as recited in claim 3 wherein said pump is driven by a stepper motor.
5. A surface energy meter as recited in claim 4 wherein said means for determining said volume includes a means for counting a number of steps of said stepper motor.
6. A surface energy meter as recited in claim 1 wherein said means for relating includes a stored value for a surface energy of said material.
7. A surface energy meter as recited in claim 1 wherein said means for relating includes a stored value for surface tension of said electrically conductive fluid.
8. A surface energy meter as recited in claim 7 wherein said stored value for said electrically conductive fluid ranges from 18 to 85 dynes per centimeter.
9. A surface energy meter as recited in claim 1 wherein said means for dispensing and said two spaced apart electrodes are both contained in a probe, said probe being positionable on said surface of said material.
10. A method for determining the surface energy of a material, comprising the steps of:
    dispensing a first volume of an electrically conductive fluid having a known surface tension onto a surface of a first material at a point centrally located between two spaced apart electrodes, said first volume providing an electrical pathway between said two spaced apart electrodes; and
    calculating a first surface energy of said first material from said first volume of said electrically conductive fluid.
11. A method as recited in claim 10 wherein said step of calculating includes the steps of:
    determining a second volume of said electrically conductive fluid having said known surface tension which is required to provide an electrical pathway between said two spaced apart electrodes when said electrically conductive fluid is dispensed onto a surface of a second material having a known second surface energy;
    determining a third volume of said electrically conductive fluid having said known surface tension which is required to provide an electrical pathway between said two spaced apart electrodes when said electrically conductive fluid is dispensed onto a surface of a third material having a known third surface energy; and
    computing said first surface energy from said first, second and third volumes of said electrically conductive fluid and said second and third surface energies.
12. A method as recited in claim 11 wherein said steps of determining said second and third volumes of said electrically conductive fluid having said known surface tension are performed in advance of said step of determining said first volume of said electrically conductive fluid having said known surface tension and are stored in a memory for use during said computing step.
13. A method for determining the surface tension of a fluid, comprising the steps of:
    assuring that a first fluid having a surface tension to be measured is electrically conductive;
    dispensing a first volume of said first fluid onto a surface of a material having a known surface energy at a point centrally located between two spaced apart electrodes, said first volume providing an electrical pathway between said two spaced apart electrodes; and
    calculating a first surface tension of said first fluid from said first volume.
14. A method as recited in claim 13 wherein said step of calculating includes the steps of:
    determining a second volume of a second electrically conductive fluid having a known second surface tension which is required to provide an electrical pathway between said two spaced apart electrodes when said second electrically conductive fluid is dispensed onto said surface of said material having said known surface energy;
    determining a third volume of a third electrically conductive fluid having a known third surface tension which is required to provide an electrical pathway between said two spaced apart electrodes when said third electrically conductive fluid is dispensed onto said surface of said material having said known surface energy; and computing said first surface tension from said first, second and third volumes of said first, second and third electrically conductive fluids and said known surface energy of said material.

15. A method as recited in claim 14 wherein said steps of determining said second and third volumes of said second and third electrically conductive fluids having said known surface tensions are performed in advance of said step of determining said first volume of said first fluid, and are stored in a memory for use during said computing step.

* * * * *